(12) United States Patent  (10) Patent No.: US 9,297,738 B2
Strandell  (45) Date of Patent: Mar. 29, 2016

(54) SYSTEM AND METHOD FOR MONITORING ENVIRONMENTAL WEAKENING OF COMPONENTS BY MONITORING ATOMIC HYDROGEN PERMEATION

(75) Inventor: Ingemar Strandell, Sävedalen (SE)

(73) Assignee: AKTIEBOLAGET SKF, Gothenburg (SE)

( * ) Notice: Subject to any disclaimer, the term of this patent is extended or adjusted under 35 U.S.C. 154(b) by 261 days.

(21) Appl. No.: 14/130,672

(22) PCT Filed: Jun. 21, 2012

(86) PCT No.: PCT/SE2012/000097
§ 371 (c)(1),
(2), (4) Date: Jan. 2, 2014

(87) PCT Pub. No.: WO2013/012364
PCT Pub. Date: Jan. 24, 2013

(65) Prior Publication Data
US 2014/0157874 A1 Jun. 12, 2014

(51) Int. Cl.
*G01N 15/08* (2006.01)
*F16C 19/52* (2006.01)

(52) U.S. Cl.
CPC ............ *G01N 15/0826* (2013.01); *F16C 19/52* (2013.01); *F16C 19/522* (2013.01); *F16C 19/525* (2013.01); *F16C 2233/00* (2013.01)

(58) Field of Classification Search
CPC ...... F16C 19/52; F16C 19/522; F16C 19/525; F16C 2233/00; G01N 15/0826; G01N 15/08; G01N 17/02; G01M 3/22; G01M 3/223; G01M 3/222; Y10T 436/22
See application file for complete search history.

(56) References Cited

U.S. PATENT DOCUMENTS

| | | | |
|---|---|---|---|
| 2005/0045248 A1* | 3/2005 | Otani | C21D 1/78 148/219 |
| 2005/0205163 A1* | 9/2005 | Ohki | C21D 1/78 148/219 |
| 2010/0021097 A1* | 1/2010 | Uchida | B65G 39/09 384/492 |

OTHER PUBLICATIONS

Mishael, "Practical Applications of Hydrogen Permeation Monitoring", 2004 NACE, pp. 1-12.*
Hearn, E.J.. (1997). Mechanics of Materials, vol. 2—An Introduction to the Mechanics of Elastic and Plastic Deformation of Solids and Structural Materials (3rd Edition). (pp. 381-383). Elsevier.*

* cited by examiner

Primary Examiner — Daniel S Larkin
Assistant Examiner — Jamar Ray
(74) Attorney, Agent, or Firm — Bryan Peckjian; SKF USA Inc. Patent Dept.

(57) ABSTRACT

A system comprising at least one component for an application in which the at least one component is subjected to Hertzian stress or alternating Hertzian stress or altering Hertzian stress in combination with structural stress, and at least one sensor that is arranged in situ to monitor atomic hydrogen permeation through at least part of the at least one component.

21 Claims, 2 Drawing Sheets

SYSTEM AND METHOD FOR MONITORING ENVIRONMENTAL WEAKENING OF COMPONENTS BY MONITORING ATOMIC HYDROGEN PERMEATION

CROSS REFERENCE TO RELATED APPLICATION

This application is a National Stage application claiming the benefit of International Application Number PCT/SE2012/000097 filed on 21 Jun. 2012, which claims the benefit of Swedish Patent Application Serial Number 1100509-7, filed on 1 Jul. 2011.

TECHNICAL FIELD

The present invention concerns a system and method for monitoring environmental weakening of at least one component for an application in which it is subjected to stress or alternating Hertzian stresses or combined structural and Hertzian stresses.

BACKGROUND OF THE INVENTION

Root cause analysis is a class of problem solving methods aimed at identifying the root cause(s) of a problem or event in order to create effective corrective actions that will prevent that problem or event from recurring.

Root cause analyses have successfully been used in numerous machine failure investigations.

Findings from root cause analyses can be utilized to redesign a machine improving working conditions for a failing component. Findings from root cause analyses can further be used to monitor and control root-cause parameters, such as load, temperature, electrical stray currents, lubrication failures and hydrogen diffusion flux. Redesign, monitoring and control can be used to avoid or at least reduce the risk for premature failures.

In premature failure of machines the root cause analyses involves load and strength for the failing component. This analyses start with an analysis of the machine operating conditions, the external loads, internal machine resonances, loads and operational conditions all the way down to tribology contact conditions and the detailed stress fields in the component.

The complexity of the machine systems, the large number of interacting components, uncertainties in process loads, environmental and running conditions make the stress analyses in the components difficult. The uncertainty in stress analyses depends on the static and dynamic conditions of the load. Turbo machinery such as wind mills, marine pods, pumps and fans may have running conditions for which it is difficult to estimate the real loads. Uncertainties in stress analyses are further linked to the constraints and simplifications that are often made in order speed up or even make simulations possible. Bearings in pliant structures may be poorly supported, changing the stress distributions in rings and rollers. Rolling elements may further be forced to move, skew and even partly jam causing higher stresses in reality than those derived in calculations.

Strength analysis involves investigations of components, such as bearings, gears, lubricants, houses or shafts. The conformance with specifications and tolerances are checked.

Signs for wear, smearing, galling, micropitting, spalling, plastic deformation, surface distress, cracks, wear patterns from loads contact and corrosion on the failed components are investigated. Near surface and subsurface material decay, changes in residual stress and x-ray line broadening, micro structural changes and fatigue development of components and aging of lubricants are also investigated. Signs of damage, wear, load or corrosion on adjoining components give additional information. Lack of damage on adjoining components may also provide knowledge on the machine's running conditions, its load and environmental conditions.

The failures are often detected at a late stage where initial failure mode is partly hidden behind secondary failures. Stresses, load cycles, temperature and material strength are compared to fatigue and fracture calculations. These findings are compared to the failure observations. When root cause failure analyses are non-conclusive there often remains an uncertainty in both load and stress estimates as well as in environmental weakening of the component.

Environmentally induced weakening or cracking can be found under a range of stress conditions. Cracks can be driven by embrittlement processes as well by anodic dissolution. Nasal or atomic hydrogen can sometimes be linked to environmental induced weakening and extensive crack propagation.

Environmental induced strength reduction is caused both by corrosion and tribocorosion processes.

Corrosive reactions are due to an irreversible oxidation-reduction reaction between a metal and an oxidizing agent present in the metal's environment. The oxidation of the metal is inseparably coupled to the reduction of the oxidizing agent, i.e.

Metal+oxidizing agent→oxidized metal+reducing agent

The following reactions take place:

Anode partial reaction $Fe \rightarrow Fe^{2+}+2e^-$

Cathode partial reaction $2H^+ + 2e^- \rightarrow H_2$

Overall reaction $Fe+2H^+ \rightarrow Fe^{2+}+H_2$

In the cathode reaction hydrogen gas is formed by the recombination of two hydrogen atoms, which are separately formed on the cathode surface.

$H^+ e^- \rightarrow H_{ads}$

This Volmer reaction produces an adsorbed hydrogen atom on the surface.

It is normally the rate limiting reaction. In a second step hydrogen atoms recombine into gas. Two processes are known $H_{ads}+H^+ \rightarrow H_2$ Heyrovsky reaction $H_{ads}+H_{ads} \rightarrow H_2$ Tafel reaction Alternatively, the adsorbed hydrogen can also diffuse into the metal.

$H_{ads} \rightarrow H_m$  $H_m$ Hydrogen dissolved in component,

Chemical compounds e.g. in the lubricant may reduce hydrogen recombination rates. The relation of Hm to H2 increases. The Hm content in the high strength steel matrix increases as does the risk for hydrogen embrittlement and/or increased crack growth rates. Hydrogen atoms are diffusing or trapped in reversible or irreversible traps. The nature of the trap, the temperature and the stress field determines whether a trap irreversible or reversible.

Atomic H can diffuse measurable distance into metal components. A steel plate with a thickness of 0.5 mm will be penetrated by H-diffusion within a couple of hours. Hydrogen may cause embrittlement and cracking of high strength components at a distance from its place of origin.

Humidity and water increase the risk for corrosion and tribocorrosion processes. The hydroscopity of water drives a significant amount of water in and out of lubricants. At stand still water content is increased, and during running operations the water content is reduced. Bearing life reduction of up to 100 times is seen in standstill corrosion tests.

Gear oils with high amounts of additives may for example release water (possibly including ionic compounds with polar components) during stand still. Water is surface active, and condensed or free water may be concentrated into crevasses, pits and narrow gaps between metal components, which may result in corrosion.

Tribocorrosion is a material degradation process due to the combined effect of corrosion and wear. Wear influences corrosion rates by removing passivating and corrosion protecting surface layers while corrosion changes friction, wear processes and wear rate. An additional feature of tribocorrosion in lubricated contacts is the exposure of the active metal surface to an electrolyte. Reactions with e.g. acids may form Hads. These increases further the risk for introducing atomic hydrogen Hm into the stressed components.

Root cause analysis may for example be used to reduce or eliminate the adverse effects of corrosion or tribocorrosion, which occurs in many engineering fields and which can significantly reduce the service life of machine components. Detection of nasal metal hydrogen will be an important tool in the root cause analyses. It may also be use monitor components and machines detecting environmental weakening of components and parts.

SUMMARY OF THE INVENTION

An object of the present invention is to provide a system and method for monitoring at least one metal component, such as a bearing or gear wheel, which is suitable for use in an application in which it is subjected to Hertzian stress or alternating Hertzian stress or altering Hertzian stress in combination with structural stress, i.e. the at least one component allows constrained relative motion between two or more parts of a machine, typically rotation or linear movement. The component is arranged to be in rolling, sliding and rolling, rubbing, or structural contact or any combination thereof with another component/part of a machine and is often used with lubricant, such as oil, grease or graphite. The at least one component is not intended to be used for the transportation or containment of oil, gas or any hydrocarbon fluid, i.e. the at least one component is not a pipe for example.

This object is achieved by a system comprising at least one such component and at least one sensor that is arranged in situ to monitor atomic hydrogen permeation through at least part of the at least one component.

Such a system may be used to provide an in situ analysis of the risk of hydrogen embrittlement and mechanical failure of the at least one component and thereby provide information on the service life of the at least one component. The system may also be used to identify the parts of a system, or the periods of running cycles, in which hydrogen is created.

The response time of the at least one sensor may be a few hours or more. However such in situ monitoring allows for information concerning atomic hydrogen permeation through at least part of at least one component to be obtained substantially in real time compared to systems in which root cause analysis is carried out after an event, such as component failure, has occurred. A system according to the present invention may therefore be used to forecast or predict probable events before they occur.

Such a system to measure or to identify if environmental weakening occurs in a component is of great value to identify root causes and to facilitate improvement of a machine, its design and the component's environment. The system may be used to identify a risk for environmental weakening of at least one component, to identify tribological conditions that may weaken the at least one component, to select lubricants reducing the risk for environmental weakening and to monitor the weakening of at least one component in situ.

According to an embodiment of the invention the at least one sensor is arranged to monitor the rate of atomic hydrogen permeation through at least part of the at least one component.

According to another embodiment of the invention the at least one sensor is arranged on an exterior surface of the at least one component, whereby atoms of hydrogen which enter the component material will eventually reach an exterior surface of the component where they can be measured. Alternatively, the at least one sensor is integrated into the at least one component (a hydrogen probe of the sensor may for example be inserted into a component), preferably into a low stressed part of the at least one component whereby there will be little or no disturbance of the component function.

Stress is the parameter in fatigue with the highest exponent for life reduction of high strength components. An increase in stress level in regions with high stress levels is therefore highly undesired. When the raceway region, with the Hertzian contact, is also the entry point for hydrogen there is conflict between the desire to put a sensor close to entry point and thereby reduce time constants and increase signal level and the influence of the sensor on the stress field in the high stress region. Sensor volume, shape of sensor, positioning of the sensor and the volume of material that needs to be removed by machining from the component need to carefully checked with the influence on the high stress field associated with the Hertzian contacts.

According to a further embodiment of the invention the at least one sensor is arranged to monitor atomic hydrogen permeation through at least part of the at least one component when the at least one component is in use. Alternatively or additionally, the at least one sensor is arranged to monitor atomic hydrogen permeation through at least part of the at least one component when the at least one component is not in use, but in stand still.

According to an embodiment of the invention the at least one sensor comprises at least one of the following: a pressure sensor, including a temperature sensor, a sensor based on the Devenathan output cell, an electrochemical current sensor, a sensor based on a fuel cell principle, an optical sensor with a fibre optic Bragg grating (FBG) coated with a palladium film (whereby the sensing mechanism is based on mechanical stress that is induced in the palladium film/coating when it absorbs hydrogen. The stress in the palladium film/coating stretches the film/coating and shifts the Bragg wavelength of the FBG), a semiconductor sensor (whereby a wide band gap semiconductor silicon carbide may for example be used as a catalytic gate field-effect device (Pt—SiO2-SiC) that can detect hydrogen-containing species in chemically reactive, high temperature environments). Any type of sensor may be used to monitor atomic hydrogen permeation through at least part of the at least one component.

According to another embodiment of the invention the system is arranged to provide information i.e. sensor data or information determined using sensor data, for subsequent processing and analysis and/or storage.

According to a further embodiment of the invention is arranged to prevent operation of the at least one component if/when the atomic hydrogen permeation through at least part of the at least one component reaches a predetermined threshold. A visual and/or audio warning may for example be provided to a remote or local user of the system.

According to an embodiment of the invention the system comprises a device to determine material standard potentials, applied electrical potential, temperature, electrolyte concentrations, electrolyte conductivity, availability and strength of oxidizing agents and/or the rate and density of formed surface films.

According to an embodiment of the invention the at least one sensor (i.e. a whole sensor or at least the atomic hydrogen permeation detecting part(s) of a sensor) is arranged within 500 mm, within 50 mm, within 10 mm, within 5 mm, within 2 mm or within 1 mm of a stressed region (i.e. a point, an area or a volume) within said at least one component.

The stresses in a component change with time and position. The contact stress field from rolling and sliding, structural stress fields and residual stress from manufacturing and evolving stress fields can be added together for certain positions. The stress field may be changed by the incorporation of the at least one sensor. Principal stresses at a particular position may be calculated by summing up all stress fields at that position.

The stressed volume can be defined as the volume in a component having an alternating shear stress exceeding a certain value. The value may be 200 MPa, 300 MPa, 350 MPa, 400 MPa, 500 MPa or higher.

A maximum contact stress and a mean contact stress can be defined in the Herztian contact.

The maximum shear stresses are found at a small depth below the contact. The relationship between stress parameters in idealized Hertzian contact is simple. The actual stress fields in components may need a deeper analysis using a finite element or a multigrid approach.

The incorporation of at least one sensor into a system, i.e. the utilization and positioning of a particular sensor and the removal of any material to position the sensor should not increase the stressed volume in any of the components by more than 1%, 3%, 10% or 100%, it should not increase the maximum contact stresses or the mean contact stress between rolling and sliding elements towards the contacting rings by more than 0.1%, 1%, 10% or 20% and/or it should not increase the maximum alternating shear stresses by more than 0.1%, 1%, 10% or 20%.

Maximum contact stresses may be reduced by a geometry change of a component, such as by making a hollow roller, but the highly stressed volume is then increased. The considerations regarding stress amplitude and stressed volume should be carefully considered not separately but simultaneously.

According to another embodiment of the invention the at least one sensor (i.e. a whole sensor or at least the atomic hydrogen permeation detecting part(s) of a sensor) is arranged within 500 mm, within 50 mm, within 10 mm, within 5 mm, within 2 mm or within 1 mm of a region in which atomic hydrogen permeation is expected/known to take place, such as a contact surface, a region in which a fluid, such as water or lubricant collects or corrosion/tribocorrosion occurs.

The sensor may contain stress, load, temperature, vibration, displacement, gyroscopes sensing elements. These may be positioned in the sensor volume in any combination using the same stress considerations.

The component material and heat treatment may exchanged to provide a material with higher, strength or higher fatigue strength to compensate for the life reduction of the component caused by the stress increase from the sensor position according to the above statements.

According to a further embodiment of the invention the at least one sensor (i.e. a whole sensor or at least the atomic hydrogen permeation detecting part(s) of a sensor) is arranged at a distance from a region in which atomic hydrogen permeation is expected/known to take place whereby the hydrogen diffusion time is less than 1 minute, 1 hour, 10 hours, 100 hours, 1000 or 10,000 hours.

According to an embodiment of the invention the at least one sensor (i.e. a whole sensor or at least the atomic hydrogen permeation detecting part(s) of a sensor) is arranged in at least one cavity, or an edge or a surface of said at least one component. The at least one sensor may for example be arranged in at least one cavity (such as in a cavity in a roller), or at an outer edge/surface of said at least one component.

According to an embodiment of the invention the at least one sensor (i.e. a whole sensor or at least the atomic hydrogen permeation detecting part(s) of a sensor) is arranged to monitor hydrogen permeation at a raceway of a bearing.

According to another embodiment of the invention the at least one component comprises at least part of a ball bearing, a roller bearing, a needle bearing, a tapered roller bearing, a spherical roller bearing, a toroidal roller bearing, a ball thrust bearing, a roller thrust bearing, a tapered roller thrust bearing, a wheel bearing, a traction drive, a cam or clutch system, a hub bearing unit, a slewing bearing, a roller screw, a ball screw, a gear wheel or any other machine having moving Herzian contacts.

The present invention also concerns a method for monitoring at least one component for an application in which it is subjected to alternating Hertzian stresses. The method comprises the step of providing a system according to any of the embodiments of the invention and monitoring atomic hydrogen permeation through at least part of the at least one component.

The present invention also concerns the use of a system according to any of the embodiments of the invention or a method according to any of the embodiments of the invention to monitor corrosion, tribocorrosion or a lubricant, i.e. to select a suitable lubricant or monitor the performance of a lubricant being used, and/or to schedule component maintenance and/or lubrication.

BRIEF DESCRIPTION OF THE DRAWINGS

The present invention will hereinafter be further explained by means of non-limiting examples with reference to the appended figures where.

It should be noted that the drawings have not been drawn to scale and that the dimensions of certain features have been exaggerated for the sake of clarity.

DETAILED DESCRIPTION OF EMBODIMENTS

Figure 1:
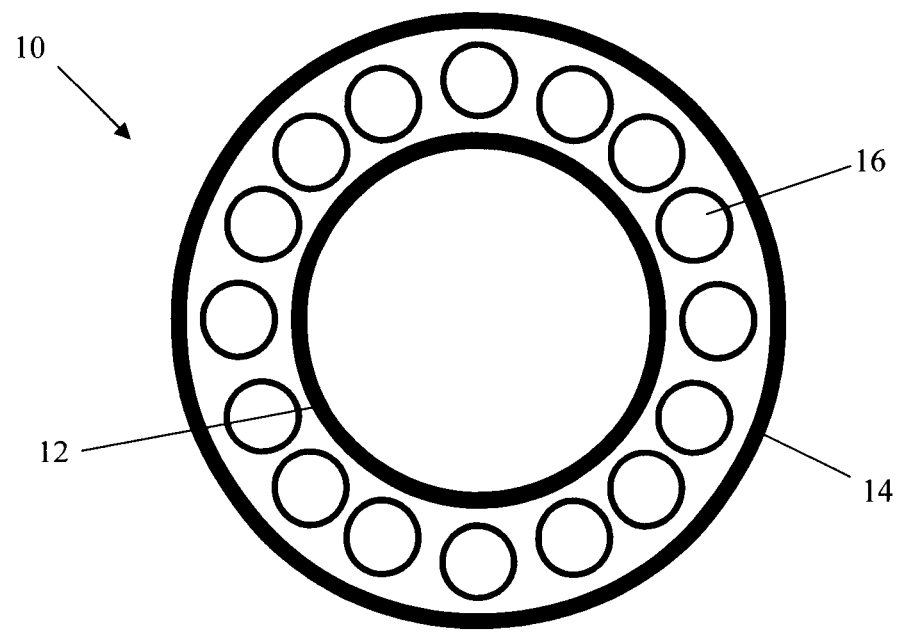
FIG. 1 shows a component constituting part of a system according to an embodiment according to the present invention.
Figure 2:
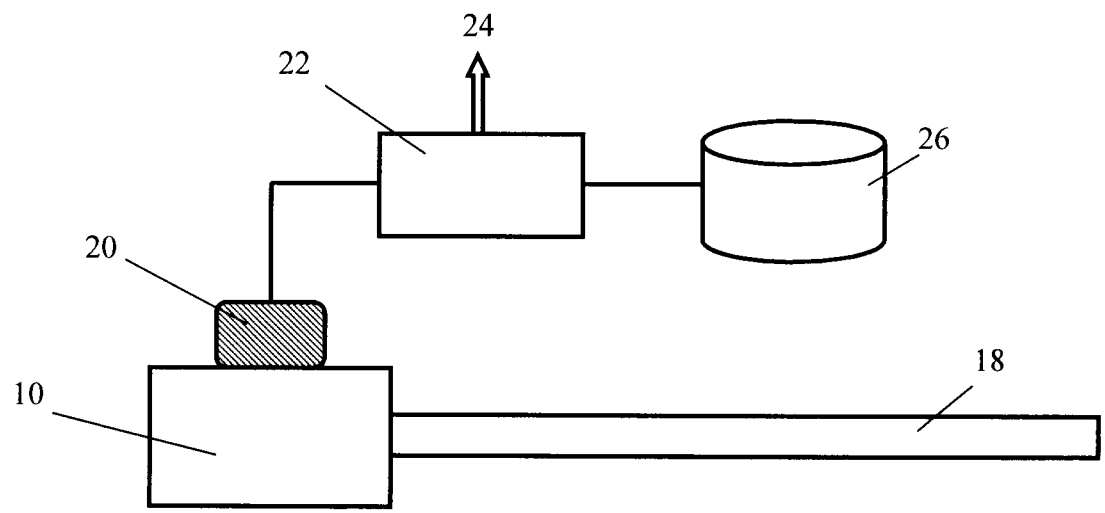
FIG. 2 shows a system according to an embodiment according to the present invention.

FIG. 1 shows a component 10 for an application in which it is subjected to alternating Hertzian stresses, namely a rolling element bearing that may range in size from 10 mm in diameter to a few meters in diameter and have a load-carrying capacity from a few tens of grams to several thousands of kilograms. The component 10 may be of any size and have any load-carrying capacity. The illustrated bearing component 10 has an inner ring 12, an outer ring 14 and a set of rolling elements 16. The inner ring 12, the outer ring 14 and/or the rolling elements 16 of the rolling element bearing 10, and preferably all of the rolling contact parts of the rolling element bearing 10 are manufactured from steel or ceramics FIG. 2 shows a system comprising at least one component 10 for an application in which it is subjected to alternating Hertzian stresses, such as at least one bearing or gear wheel arranged at the end of a shaft 18 for example.

In the illustrated embodiment a sensor 20 is arranged in situ on an exterior surface of the at least one component 10 to monitor the rate of atomic hydrogen permeation through at least part of the at least one component 10 both when the at least one component 10 is in use and when it is not in use.

The sensor 20 may comprise at least one of the following: a pressure sensor, an electrochemical current sensor, a sensor based on a fuel cell principle, an optical sensor with a fibre optic Bragg grating (FBG) coated with a palladium film, a semiconductor sensor. Micro-Electro-Mechanical Systems (MEMS) sensors, such as surface acoustic wave sensors may also be used.

The sensor 20 may for example use a hydrogen probe to detect a pressure increase in a controlled chamber over a period of time, as hydrogen passes through component material into the hydrogen probe. The pressure build-up is directly proportional to the flux of atomic hydrogen, which can be determined by implementation of the ideal gas law. The temperature needs to be known. If the volume of the hydrogen probe cavity and the cross-sectional area across which diffusion is occurring is known, the flux of atomic hydrogen may be calculated. A sensor 20 may comprise of a bleed cross/block, pressure gauge, thermometer and bleed valve. The thermometer provides a means for correcting the change in pressure readings due to fluctuations in the ambient temperature. A bleed valve may be used to relieve pressure build up at predetermined intervals so as not to exceed the pressure gauge rating of the sensor 20.

Alternatively, the sensor may detect an electrochemical current resulting from the oxidation of hydrogen under an applied potential or the current flow in an external circuit, based on a fuel cell principle, whereby hydrogen entering a miniature fuel cell causes the current flow.

According to an embodiment of the invention the electrodes/probe of a sensor 20 may comprise the same material as the component 10 being monitored.

It should be noted that a sensor 20 may be provided on one or more components 10 of a system, or on each component 10 of a system. Furthermore, a plurality of sensors 20 may be provided on a single component 10 of a system. Hydrogen permeation/creation may namely be non-homogeneous in different parts of a system or in different parts of a component 10.

The system may comprise a processing unit 22 that is arranged to provide obtained and/or calculated information 24 concerning the atomic hydrogen permeation through at least part of the at least one component 10 to a remote or local user or device by any known means. The system may also comprise a local or remote memory 26 to store information 24 concerning the atomic hydrogen permeation. The information 24 may be used to monitor corrosion, tribocorrosion or a lubricant, and/or to schedule component maintenance and/or lubrication.

The system may be arranged to prevent operation of the at least one component 10 if/when the atomic hydrogen permeation through at least part of the at least one component 10 reaches a predetermined threshold.

The system may also comprise a device to determine/measure material standard potentials, applied electrical potential, temperature, electrolyte concentrations, electrolyte conductivity, availability and strength of oxidizing agents and/or the rate and density of formed surface films. Data from these devices may also be provided to a remote or local user or device and/or stored by the system.

A sensor 20 may be arranged to collect data continuously, periodically or during predetermined periods only, for example during stand still periods or during running periods with high speed and low loads.

Figure 3:
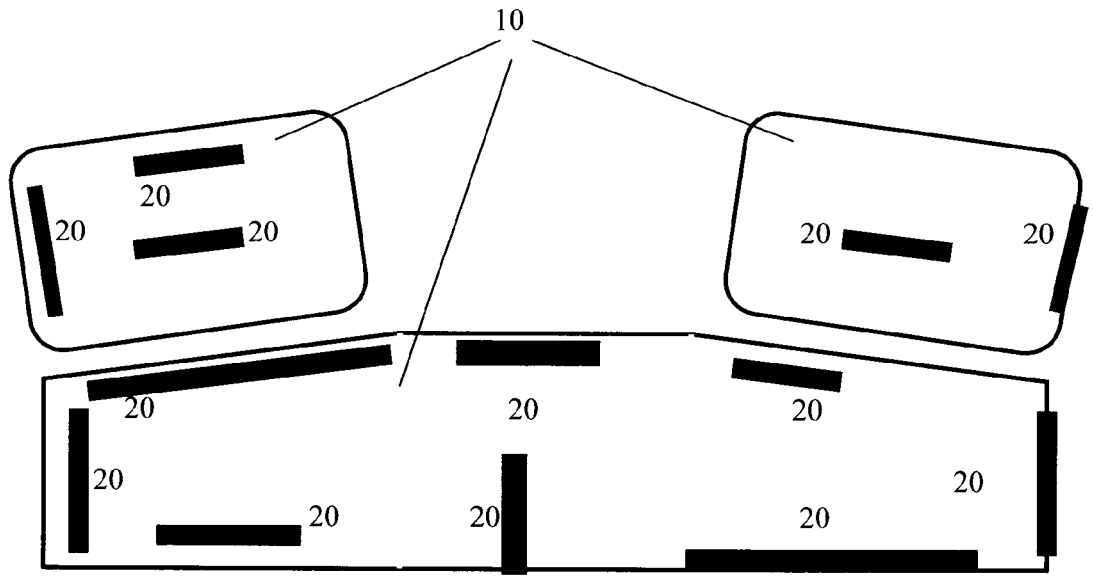
FIG. 3 shows a system according to an embodiment according to the present invention.

FIG. 3 shows a system according to an embodiment of the invention in cross section, namely a bearing component 10. The shaded areas 20 show positions in which at least one sensor 20 arranged in situ to monitor atomic hydrogen permeation through at least part of said at least one component 10 may be arranged.

For example at least one sensor (i.e. a whole sensor or at least the atomic hydrogen permeation detecting part(s) of a sensor) 20 may be arranged within 500 mm, within 50 mm, within 10 mm, within 5 mm, within 2 mm or within 1 mm of a stressed region (i.e. a point, an area or a volume) within said at least one component.

The stressed volume can be defined as the volume in a component having alternating shear stress amplitude exceeding 200 MPa, 300 MPa, 350 MPa, 400 MPa, 500 MPa or higher. The sensor and the material removed to position the sensor should not increase the stressed volume in any of the components by more than 1%, 3%, 10% or 100%, should not increase the maximum contact stresses or the mean contact stress between rolling and sliding elements towards the contacting rings by more than 0.1%, 1%, 10% or 20% and should not increase the maximum alternating Hertzian shear stresses by more than 0.1%, 1%, 10% or 20%.

According to an embodiment of the invention the at least one sensor (i.e. a whole sensor or at least the atomic hydrogen permeation detecting part(s) of a sensor) 20 is arranged within 500 mm, within 50 mm, within 10 mm, within 5 mm, within 2 mm or within 1 mm of a region in which atomic hydrogen permeation is expected/known to take place, such as a contact surface, a region in which a fluid, such as water or lubricant collects or corrosion/tribocorrosion occurs.

The sensor may contain stress, load, temperature, vibration, displacement, gyroscopes sensing elements. These may be positioned in at least one sensor volume in any suitable manner.

Figure 4:
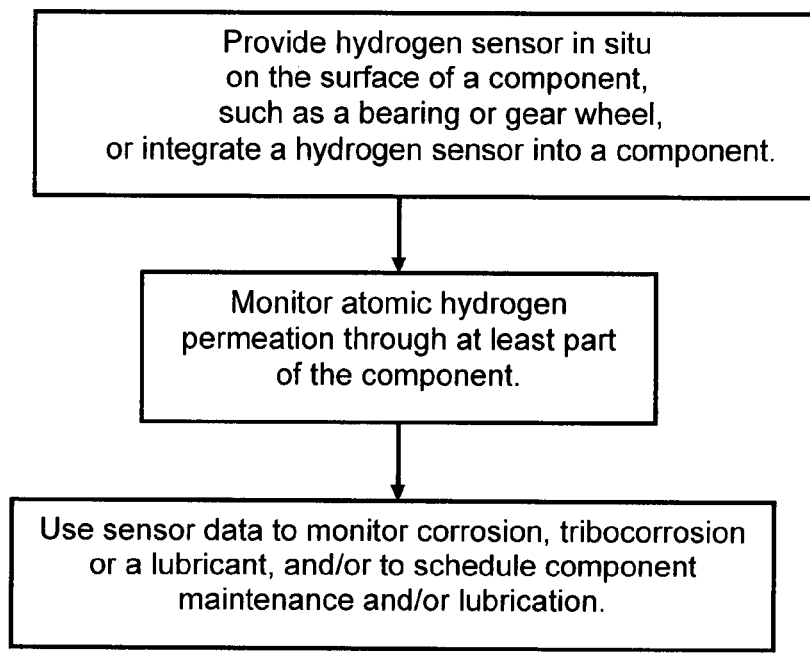
FIG. 4 is a flow diagram outlining the steps of a method according to an embodiment of the present invention.

FIG. 4 is a flow diagram outlining the steps of a method according to an embodiment of the present invention. The method comprises the steps of providing a system with at least one component, such as a bearing or gear wheel, for an application in which it is subjected to alternating Hertzian stresses, with a hydrogen sensor, i.e. a sensor monitoring atomic hydrogen permeation through at least part of the at least one component, and monitoring the hydrogen permeation through at least part of the at least one component. The sensor data or information derived from the sensor data may be used to monitor corrosion, tribocorrosion or a lubricant, and/or to schedule component maintenance and/or lubrication and predict component failure.

Further modifications of the invention within the scope of the claims would be apparent to a skilled person.

The invention claimed is:

1. A system comprising at least one component for an application in which said at least one component is subjected to one of a Hertzian stress, alternating Hertzian stress, or altering Hertzian stress in combination with structural stress, and at least one sensor, wherein said at least one sensor is arranged in situ to monitor atomic hydrogen permeation through at least part of said at least one component.

2. The system according to claim 1, wherein said at least one sensor is arranged to monitor the rate of atomic hydrogen permeation through at least part of said at least one component.

3. The system according to claim 1, wherein said at least one sensor is arranged on an exterior surface of said at least one component.

4. The system according to claim 1, wherein said at least one sensor is integrated into said at least one component.

5. The system according to claim 1, wherein said at least one sensor is arranged to monitor atomic hydrogen permeation through at least part of said at least one component when said at least one component is in use.

6. The system according to claim 1, wherein said at least one sensor is arranged to monitor atomic hydrogen permeation through at least part of said at least one component when said at least one component is not in use.

7. The system according to claim 1, wherein said at least one sensor comprises at least one of the following: a pressure sensor, an electrochemical current sensor, a sensor based on a fuel cell principle, an optical sensor with a fibre optic Bragg grating (FBG) coated with a palladium film, and a semiconductor sensor a MEMS sensor.

8. The system according to claim 1, wherein said system is arranged to provide information concerning the atomic hydrogen permeation through at least part of said at least one component.

9. The system according to claim 1, wherein said system is arranged to prevent operation of said at least one component if/when the atomic hydrogen permeation through at least part of said at least one component reaches a predetermined threshold.

10. The system according to claim 1, further comprising a device to determine material standard potentials, applied electrical potential, temperature, electrolyte concentrations, electrolyte conductivity, availability and strength of oxidizing agents and/or the rate and density of formed surface films.

11. The system according to claim 1, wherein said at least one sensor is arranged within 500 mm of a stressed region within said at least one component.

12. The system according to claim 1, wherein said at least one sensor is arranged in such way that one of the maximum contact stresses or the mean contact stress between rolling and sliding elements of said at least one component are not increased by more than 20%.

13. The system according to claim 1, wherein said at least one sensor is arranged in such way that the maximum Herzian shear stress in said stressed region is not increased by more than 20%.

14. The system according to claim 1, wherein said at least one sensor is arranged in such way that the incorporation of said at least one sensor into said system does not increase a stressed volume by more than 100%.

15. The system according to claim 1, wherein said at least one sensor is arranged within 500 mm of a region in which atomic hydrogen permeation is expected/known to take place.

16. The system according to claim 1, wherein said at least one sensor is arranged at a distance from a region in which atomic hydrogen permeation is expected/known to take place whereby the hydrogen diffusion time is less than 10,000 hrs.

17. The system according to claim 1, wherein said at least one sensor is arranged in at least one of: at least one cavity, an edge, or a surface of said at least one component.

18. The system according to claim 1, wherein said at least one sensor is arranged to monitor hydrogen permeation at a raceway of a bearing.

19. The system according to claim 1, wherein said at least one component comprises at least one of: a ball bearing, a roller bearing, a needle bearing, a tapered roller bearing, a spherical roller bearing, a toroidal roller bearing, a ball thrust bearing, a roller thrust bearing, a tapered roller thrust bearing, a wheel bearing, a hub bearing unit, a slewing bearing, a ball screw, a gear wheel.

20. A method for monitoring at least one component for an application, the method comprising steps of:
    installing a system comprising said at least one component for said application in which said at least one component is subjected to one of: a Hertzian stress, an alternating Hertzian stress, or an altering Hertzian stress in combination with a structural stress, and at least one sensor,
    wherein said at least one sensor is arranged in situ to monitor atomic hydrogen permeation through at least part of said at least one component, and
    monitoring atomic hydrogen permeation through at least part of said at least one component.

21. The method for monitoring at least one component for an application according to claim 20, in which the at least one component is subjected to alternating Hertzian stresses, the method further comprising a step of:
    monitoring at least one of:
        corrosion,
        tribocorrosion or a lubricant, and
        schedule of component maintenance and/or lubrication.

* * * * *